United States Patent
Galloway et al.

(10) Patent No.: US 12,226,236 B2
(45) Date of Patent: Feb. 18, 2025

(54) SYSTEMS AND METHODS OF ANALYTE MEASUREMENT ANALYSIS

(71) Applicant: AliveCor, Inc.

(72) Inventors: Conner Daniel Cross Galloway, Sunnyvale, CA (US); Alexander Vainius Valys, Sunnyvale, CA (US); David E. Albert, Oklahoma City, OK (US); Frank Losasso Petterson, Los Altos Hills, CA (US)

(73) Assignee: AliveCor, Inc., Mountain View, CA (US)

( * ) Notice: Subject to any disclaimer, the term of this patent is extended or adjusted under 35 U.S.C. 154(b) by 347 days.

(21) Appl. No.: 17/382,217

(22) Filed: Jul. 21, 2021

(65) Prior Publication Data
US 2021/0345972 A1 Nov. 11, 2021

Related U.S. Application Data

(63) Continuation of application No. 15/842,419, filed on Dec. 14, 2017, now Pat. No. 11,103,194.
(Continued)

(51) Int. Cl.
*A61B 5/00* (2006.01)
*A61B 5/145* (2006.01)
(Continued)

(52) U.S. Cl.
CPC ........ *A61B 5/7267* (2013.01); *A61B 5/14546* (2013.01); *A61B 5/332* (2021.01);
(Continued)

(58) Field of Classification Search
CPC ..... A61B 5/7267; A61B 5/044; A61B 5/0452; A61B 5/14546; A61B 5/746;
(Continued)

(56) References Cited

U.S. PATENT DOCUMENTS 6,263,238 B1   7/2001   Brewer et al.
8,948,854 B2   2/2015   Friedman et al.
(Continued)

FOREIGN PATENT DOCUMENTS

IL   224207   5/2016
WO   2015/048514 A1   4/2015
(Continued)

OTHER PUBLICATIONS

International Search Report and Written Opinion received Feb. 15, 2018 for International Application No. PCT/US2017/066500.
(Continued)

*Primary Examiner* — Rex R Holmes
(74) *Attorney, Agent, or Firm* — Caldwell Intellectual Property Law

(57) ABSTRACT

Disclosed are systems for non-invasively determining a measurement of an analyte. The systems include an electrocardiogram sensor and a processing device operatively coupled to the electrocardiogram sensor. The processing device can execute instructions to receive electrocardiogram data from the electrocardiogram sensor and apply a machine learning model, wherein the machine learning model has been trained based on previous electrocardiogram data associated with a subject and source of an analyte measurement associated with the subject. The system may also determine an indication of a level of the analyte based on the electrocardiogram data.

18 Claims, 7 Drawing Sheets

Related U.S. Application Data

(60) Provisional application No. 62/457,713, filed on Feb. 10, 2017, provisional application No. 62/434,339, filed on Dec. 14, 2016.

(51) Int. Cl.
| | | |
|---|---|---|
| A61B 5/332 | (2021.01) | |
| A61B 5/339 | (2021.01) | |
| A61B 5/349 | (2021.01) | |
| G16H 40/63 | (2018.01) | |
| G16H 50/20 | (2018.01) | |
| G16H 50/70 | (2018.01) | |

(52) U.S. Cl.
CPC .............. *A61B 5/339* (2021.01); *A61B 5/349* (2021.01); *G16H 40/63* (2018.01); *G16H 50/20* (2018.01); *G16H 50/70* (2018.01); *A61B 5/14532* (2013.01); *A61B 5/4845* (2013.01); *A61B 5/4848* (2013.01); *A61B 5/746* (2013.01)

(58) Field of Classification Search
CPC . A61B 5/4848; A61B 5/14532; A61B 5/4845; A61B 5/0404; G16H 50/20; G16H 40/63; G16H 50/70
See application file for complete search history.

(56) References Cited

U.S. PATENT DOCUMENTS

| | | |
|---|---|---|
| 9,307,921 B2 | 4/2016 | Friedman et al. |
| 9,414,786 B1 | 8/2016 | Brockway et al. |
| 9,907,478 B2 | 3/2018 | Friedman et al. |
| 2008/0103403 A1 | 5/2008 | Cohen |
| 2010/0332142 A1* | 12/2010 | Shadforth ............ A61B 5/4833 600/300 |
| 2016/0256063 A1 | 9/2016 | Friedman et al. |
| 2017/0312614 A1 | 11/2017 | Tran et al. |
| 2018/0350468 A1* | 12/2018 | Friedman ........... A61B 5/14546 |

FOREIGN PATENT DOCUMENTS

| | | |
|---|---|---|
| WO | 2016/038585 A1 | 3/2016 |
| WO | 2017/091736 A1 | 6/2017 |
| WO | 2018/049402 A1 | 3/2018 |

OTHER PUBLICATIONS

Invitation to Pay Additional Fees received Apr. 17, 2018 for International Application No. PCT/US2018/017880.
Porter et al., "Prediction of Hyperkalemia in Dogs from Electrocardiogramameters Using an Artificial Neural Network", Academic Emergency Medicine, vol. 8, No. 6, Jun. 2001, pp. 599-603.
Supratak et al., "Survey on Feature Extraction and Applications on Biosignals" ECCV 2016 Conference, Springer International Publishing, Dec. 10, 2016, pp. 161-182.
Tzeng et al., "Predicting Hyperkalemia by the Use of a 12-Lead Temporal Spatial Electrocardiogramical Evaluations and Model Simulations", Computers in Cardiology, Lyon, France, IEEE, Piscataway, NJ, USA, Sep. 25, 2005, pp. 215-218.
Wu et al., "Predicting Hyperkalemia by a Two-Staged Artificial Neural Network", Computers in Cardiology, New York, NY, US, IEEE, vol. 30, Sep. 21, 2003, pp. 433-436.
Response to Office Action filed Feb. 28, 2018 in U.S. Appl. No. 15/025,158.
U.S. Appl. No. 62/258,956, filed Nov. 23, 2015.
U.S. Appl. No. 62/401,044, filed Sep. 28, 2016.

* cited by examiner

SYSTEMS AND METHODS OF ANALYTE MEASUREMENT ANALYSIS

CROSS-REFERENCE TO RELATED APPLICATIONS

This application is a continuation of U.S. application Ser. No. 15/842,419, filed Dec. 14, 2017, now U.S. Pat. No. 11,103,194 B2, issued Aug. 31, 2021, entitled "SYSTEMS AND METHODS OF ANALYTE MEASUREMENT ANALYSIS," which claims the benefit of U.S. Provisional Application No. 62/457,713, filed on Feb. 10, 2017 and U.S. Provisional Application No. 65/434,339 filed on Dec. 14, 2016, the entire contents of each are hereby incorporated by reference.

BACKGROUND

Electrolytes are tightly regulated within the healthy mammalian body. For example, potassium, magnesium and calcium are essential electrolytes used by the body in numerous physiological processes, where a relatively small deviation in electrolyte concentration outside of a normal range may lead to serious complications within an individual. For example deviation of potassium concentration, hypokalemia and hyperkalemia, is associated with cardiac arrest.

Electrolytes within the mammalian body may be monitored invasively through, for example, drawing a blood sample from an individual and analyzing the blood sample for the electrolyte level within the sample.

DETAILED DESCRIPTION

Figure 1:
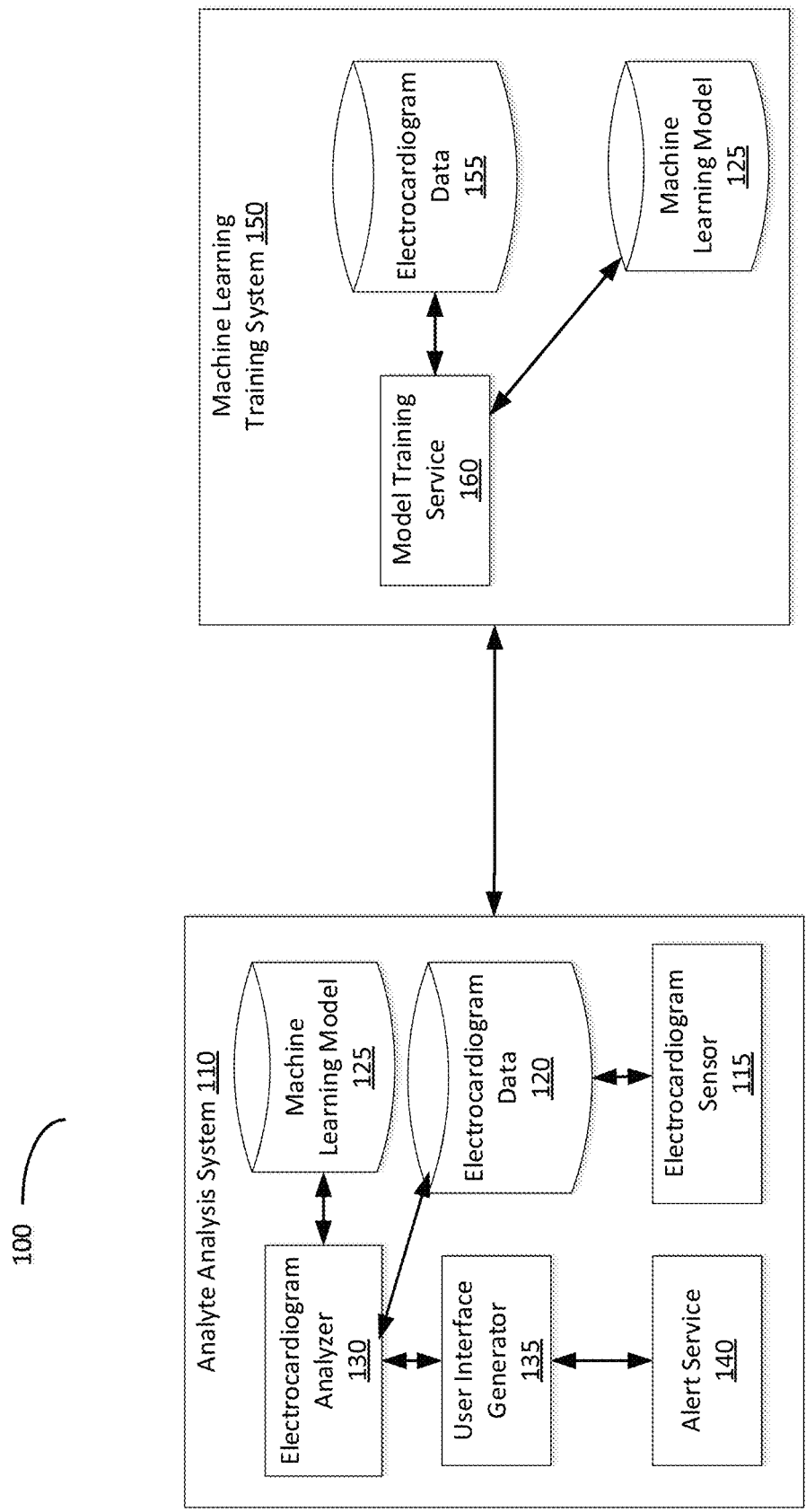
FIG. 1 illustrates an example system to provide analyte measurement as discussed herein, according to aspects of the disclosure.

Described herein are non-invasive devices and techniques for monitoring a level of a substance within the body of an individual. The non-invasive technique described herein includes sensing a biosignal such as an electrocardiogram of an individual and analyzing the biosignal to determine a level of a substance within the body of the individual based on the analysis of the biosignal.

In some embodiments, a substance that is non-invasively determined comprises an electrolyte such as, for example, potassium, magnesium, or calcium, other substances within a body may also be determined from analysis of an electrocardiogram. For example, a level of glucose within the body of an individual, a level of a pharmaceutical or pharmaceutical byproduct within the body of an individual, a level of alcohol or other drugs, or other substances may be determined from analysis of an electrocardiogram or other biological signals.

An electrocardiogram may be described with a number of features. Some of the common features viewed during analysis of an electrocardiogram include a P wave, a QRS wave, and a T wave. Other features may also be viewed in different electrocardiograms of different individuals. The level of certain analytes within the blood of an individual (e.g. a serum potassium level) may have an effect on that individual's electrocardiogram. For example, certain analytes may change a slope, amplitude, duration, smoothness, or other characteristics of a feature of an electrocardiogram signal.

These effects on the morphology of an electrocardiogram are sometimes subtle and not directly obvious to the human eye. In addition, changes to an electrocardiogram may not correspond to changes in an obvious component of the electrocardiogram waveform (e.g. a QRS complex), but may instead correspond to one or more correlations between one or more small and/or apparently unrelated features of the electrocardiogram. Accordingly, applying techniques to individual waveforms may provide additional insight into an electrocardiogram that isn't immediately obvious by simply looking at it.

Furthermore, individuals may have different electrocardiogram features. For example, certain persons may have a T wave that is inverted compared to other persons, different average amplitudes of features, slopes of features, or other changes that vary across populations. The correlation between certain features or combinations of features with analyte levels may vary across individuals. Accordingly, simple mathematical models that are built to estimate blood analytes across a population may not be accurate enough for clinical or other use.

In order to provide improved accuracy into concentrations in an individual's blood, in some embodiments, a machine learning model may be applied to electrocardiogram readings from an individual. In some embodiments, a machine learning model may be trained on an individual's electrocardiogram data at times when a target analyte level is known or is easily predictable. For example, an analyte level may be measured by drawing blood, or other techniques, at different times. The analyte level across a continuous time spectrum may then be determined between the different times due to one or more predictable mathematical models. For example, an exponential decay of an analyte level between certain time periods may be used to estimate analyte levels. In other situations, a linear regression (or other regression model), or extrapolation techniques, may be used to estimate analyte levels within a time interval.

In other situations, a model can be used to predict the analyte level in response to a known stimulus. For instance, a pharmacokinetic model can be used to estimate analyte levels of a pharmaceutical in the time following ingestion of a known quantity of pharmaceutical in controlled conditions. Such model could incorporate multiple parameters: e.g. body weight, blood measurements, urine measurements, metabolic rate, etc.

The known analyte levels, whether from continuous direct measurement or derived from measurements at several points, may be combined with continuous measurement of an individual's electrocardiogram to train a machine learning algorithm. For example, measurement of the individual's electrocardiogram may be used as an input to a machine learning system with the analyte levels measured for the individual as labeled output data. Based on the output data, the machine learning model may be updated to improve output characteristics.

In some embodiments, the individual's electrocardiogram may be read by an electrocardiogram sensor as a number of samples. For example, the electrocardiogram may represent data read in over a period of time. In some embodiments, the electrocardiogram may operate at approximately 300 hertz, 60 hertz, 1000 hertz, or at another frequency of sampling to provide accurate data for the electrocardiogram. The electrocardiogram data may be read into the machine learning model in intervals of time. For example, the electrocardiogram data may be used as a 10 second input of data. In some embodiments, rather than a continuous string of data, an average heartbeat may be determined by detecting each heartbeat present in the electrocardiogram signal, aligning each heartbeat based on a common feature such as the R-wave, and averaging each beat to produce an average amplitude at different parts of the beat. This may reduce noise or signal artifact present in the electrocardiogram recording.

While training the machine learning model can be performed with a number of techniques, as further discussed below, generally the electrocardiogram data will be input with labeled analyte levels. Depending on the type of machine learning model, the electrocardiogram data may then be processed by a set of mathematical operations (e.g. addition, multiplication, convolution) involving weight matrices in a number of levels of the machine learning model. After processing, the machine learning model may then generate an output. Based on the output compared to the label for the data, the machine learning model may be updated. For example, weight matrices may be updated using back propagation to better approximate the labeled data during a next processing stage.

The process of training the machine learning model may be repeated with each segment of the electrocardiogram data at different time using the labeled analyte data. The process may be repeated through all the electrocardiogram data multiple times until the outputs of the machine learning model are within a threshold of accuracy. For example, the threshold may be set to be within a set amount of the measured values at each point in time. The threshold may also be set such that it is within a threshold of a measured value at least at a threshold amount of time.

While various machine learning models may be used, in some embodiments, a convolutional neural net, a recurrent neural net, or a combination of a convolutional neural net and a recurrent neural net may be used. For example, a machine learning model may include 4 convolutional layer and 2 fully connected layers. In some embodiments, fewer or additional layers of different types may also be used. Furthermore, in some embodiments, drop out matrices, skip connection, max pooling, or other techniques may be used.

After training, the machine learning model may be applied to various electrocardiogram data for a user. For example, after training over a period of time without known blood analyte levels, which may be invasively captured, a user may use a simple electrocardiogram reading to determine a concentration level of the particular analyte in the individual's blood. In some embodiments, the electrocardiogram may be applied as an input to the machine learning model in the same or similar manner as during training. For example, if ten second intervals of electrocardiogram data were used to train a machine learning system, the same type of electrocardiogram data may be used when applying the machine learning model to determine an analyte level for an individual. Similarly, if an average heartbeat was used over an interval, the same average heartbeat pre-processing may be applied when applying the machine learning model.

In some embodiments, training of a machine learning model may be performed at a computer or server capable of large amounts of data processing. For example, a computing or server system may be used for multiple individuals to train multiple machine learning models for each individual. However, in some embodiments, training of a machine learning model may be performed on an individual's personal computer, mobile device, smart watch or the like. In some embodiments after training, a machine learning model may be applied by a different computer system than used by training. For example, a computing system or server system may be used to train a machine learning model for an individual, however, after training, the machine learning model may be applied on the individual's personal computer, mobile device, smart watch, or the like. Of course, in some implementations, different servers, computer systems, personal computers, mobile devices, or the like may be used to perform any tasks as described herein.

Figure 7:
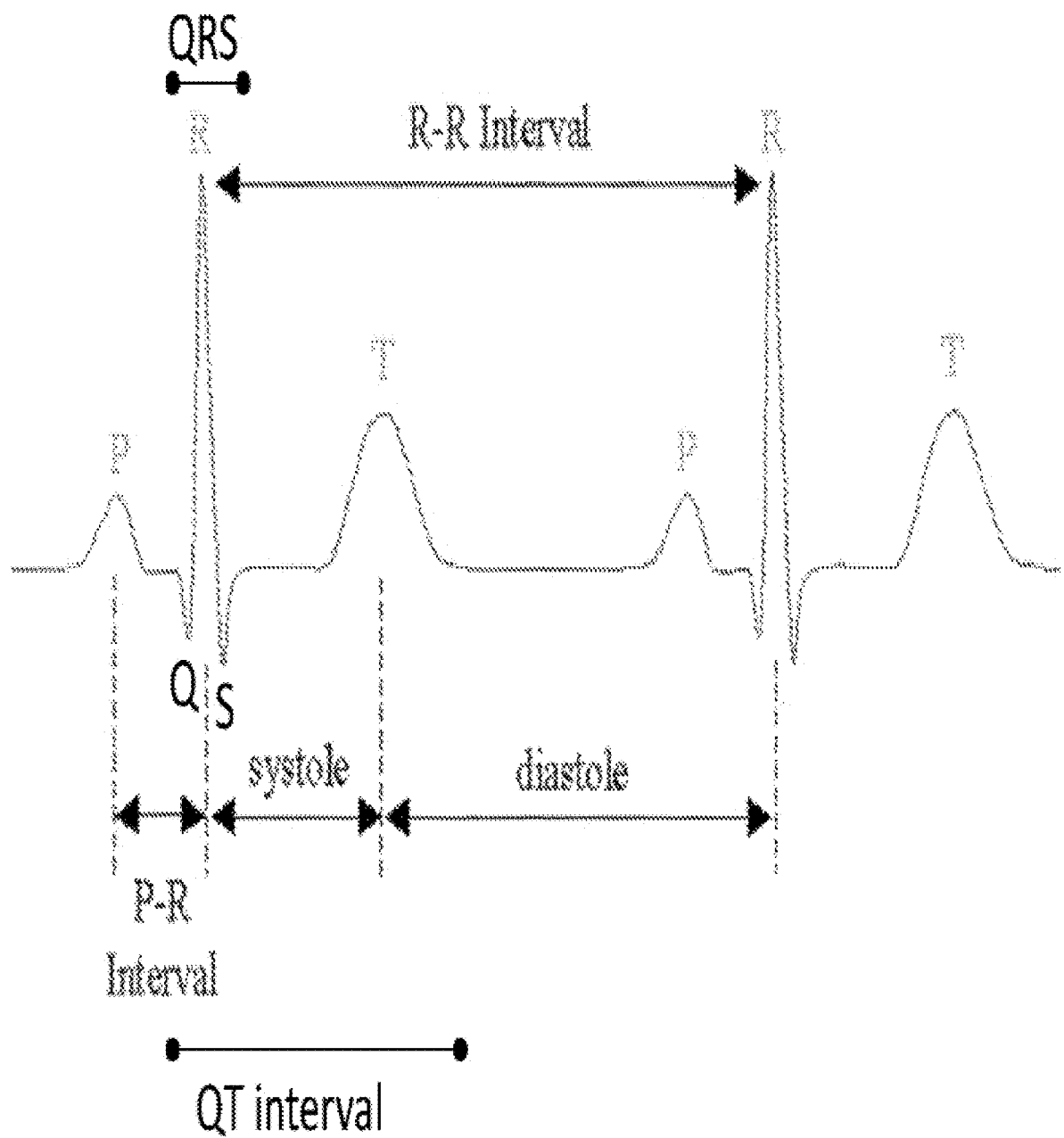
FIG. 7 illustrates example electrocardiogram signals, according to aspects of the disclosure.

For reference, FIG. 7 shows a general electrocardiogram having standard features. For example, the electrocardiogram shows two measured beats. Each beat has a P-wave, a QRS complex, and a T-wave. Each segment has different amplitudes and slopes at various points. As shown, the R-R interval shows the length between peaks of the beats. The electrocardiogram also shows other intervals including a P-R interval, a systole period, a diastole period and a QT interval. Although the elements of these features may be built in to the machine learning model, they are not necessarily individually analyzed by the model. For example, the machine learning model may learn features of relations between features during training that are different than those shown. Furthermore, as discussed above, certain individual's may have different features than shown in a typical electrocardiogram. For example, some individuals may not have a T-wave, may have a bi-phasic T-wave, an inverted T-wave or other features. Accordingly, although described as learning features indicating an analyte level for an individual, such learning should not be attributed to any specific features of an individual's electrocardiogram.

FIG. 1 illustrates an example analyte measurement system 100 that supports the analysis of electrocardiograms or other biosignals as described herein. The analyte measurement system 100 may include an analyte analysis system 110 and a machine learning training system 150. Although shown as separate components, in some embodiments, the analyte analysis system 100 and the machine learning training system 150 may be part of the same computer system. In some embodiments, the analyte analysis system 110 and the machine learning training system 150 may be remote components connected over a network. For example, the analyte analysis system 110 may be located on a personal device such as a mobile device, personal computer, smart watch, or the like. The machine learning training system may be located on the same device as the analyte analysis system 110 or on a remote device such as a central server.

In some embodiments, there may be fewer or additional components than shown in FIG. 1. For example, in some embodiments there may be additional analyte analysis systems 110 that are associated with different individuals. Furthermore, while an electrocardiogram sensor 115 is shown as part of analyte analysis system 100, in some embodiments, there may be different electrocardiogram sensors (not shown) that are used in different parts of training and application stages of a machine learning model.

The machine learning training system 150 may include a model training service 160 an electrocardiogram data store 155 and a machine learning model 125. The electrocardiogram data store 155 may include electrocardiogram data associated with an individual that was taken over a period of time. In some embodiments, the electrocardiogram data 155 may include additional data associated with additional individuals. For example, the machine learning training service 150 may train additional machine learning models associated with additional individuals.

In some embodiments, the electrocardiogram data store 155 may further include labeled data indicating analyte levels for a target analyte at different times during which the electrocardiogram data was taken. Accordingly, the electrocardiogram data store 155 may include data to train a machine learning model 125. The electrocardiogram data store 155 may include electrocardiogram data over a period of time including minutes, hours, or longer. In some embodiments, the electrocardiogram data store 155 may include data associated with a set procedure or activity. For example, the electrocardiogram data store 155 may include data that is associated with dialysis, surgery, exercise, eating, or the like. Accordingly, analyte levels may be expected to change at a predictable rate during such processes and a model for the change during this process can provide accurate labels for different samples of the electrocardiogram data.

In some embodiments, the electrocardiogram data 155 may include electrocardiogram data for an individual associated with the analyte analysis system 110. For example, the electrocardiogram data 155 may receive data from analyte analysis system 110 that was generated by electrocardiogram sensor 115. In some embodiments, the electrocardiogram 155 may be generated by a different electrocardiogram sensor (not shown).

In some embodiments, multiple electrocardiogram waveforms are averaged to form a single averaged waveform that serves as the input for the model training service 160. For example, the electrocardiogram data 155 may be pre-processed to form a set of inputs with labeled data for the model training service. Each of the inputs may be an averaged waveform of heartbeats located within a set interval of electrocardiogram data. In some embodiments, the electrocardiogram data may be stored over a complete waveform interval. However, in some embodiments, additional pre-processing may be performed such as smoothing, noise reduction, or other processing. It should be understood, however, that any recording length as well as any other lead or combination of leads selected from leads I, II, III, aVR, aVL, aVF, V1, V2, V3, V4, V5, and V6 are suitable for use as inputs to machine learning model 125.

The machine learning model 125 may start as a generic machine learning model. For example, a machine learning model set to a general population may be used as a starting model for training a machine learning model for an individual. In some embodiments, the machine learning model 125 may start with randomized values for a number of matrices within the model. The machine learning model 125 may be set with a number of convolutional layers, recurrent layers, or the like prior to training by the model training service 160.

In some embodiments, the machine learning model 125 may be a recurrent neural network. A recurrent neural network may receive sequential data as an input, such as consecutive electrocardiogram samples or beats, and then the recurrent neural network updates its internal state at every time step. In some embodiments the machine learning model may be a convolutional neural network. A convolutional neural network may include a number of convolutional layers that apply convolution operations using weight matrices and non-linearities to identify one or more features in the input data. The output of each convolutional layer may then be passed up to another layer to provide further analysis. In some embodiments, the machine learning model 125 may have a combination of recurrent and convolutional layers that identify and quantify different features in input data.

The model training service 160 may train a model for an individual having data in the electrocardiogram data store 155. In some embodiments, the model training service 160 uses automatic statistical analysis of labeled data in order to determine which features to extract and/or analyze from a sensed biosignal (e.g. an electrocardiogram). The model training service 160 may determine which features to extract and/or analyze from an electrocardiogram based on labeled electrocardiogram data 155 that it receives.

In some embodiments, the model training service 160 may be configured to receive a certain length of raw electrocardiogram data as an input and to determine an analyte level. For example, an input to the model training service 160 may be 10 seconds or more of an electrocardiogram signal from lead I of an electrocardiogram sensor 115. In some embodiments the model training service 160 may use the untrained machine learning model 125 as a function approximator, mapping a high dimensional input (the raw electrocardiogram waveform) into a real number (e.g. a blood potassium value or other analyte). Based on differences between the number generated by the machine learning model 125, the model training service 160 may update the machine learning model to better fit the labeled data.

The analyte analysis system 110 in FIG. 1 may provide data from an electrocardiogram sensor 115 to store as electrocardiogram data 120. The electrocardiogram data 120 may then be applied to machine learning model 125 by an electrocardiogram analyzer 130. The machine learning model 125 may be the same as was trained by machine learning system 150. In some embodiments, the machine learning model 125, the electrocardiogram analyzer 130, or other components of the analyte analysis system 110 may be on a separate computing system than the analyte analysis system 110. For example, the machine learning training system 150 may have one or more components of the analyte analysis system 110.

The electrocardiogram analyzer 130 may apply the machine learning model 125 by providing inputs from the electrocardiogram model 120. As discussed herein, the electrocardiogram data may be pre-processed into set interval segments, average heartbeats, smoothed, noise reduced, or otherwise provided in a set manner to the electrocardiogram analyzer. The electrocardiogram analyzer 130 may then provide the machine learning model 125 to the electrocardiogram data 120 to generate an output of an analyte concentration.

In some embodiments, a user interface generator 135 may provide the analyzed data to a user interface. For example, the user interface generator 135 may generate a user interface including one or more of an analyte output, an electrocardiogram output, additional analyte data, or a combination. For example, in some embodiments, a user interface generator 135 may provide a user interface as described with reference to FIG. 3.

While shown as including a machine learning model 125 for particular analyte analysis, in some embodiments, the analyte analysis system 110 may provide additional data for additional analyte concentration. For example, machine learning training system 150 may provide multiple machine learning models 125 for different analytes based on an individual's electrocardiogram data.

In addition, an analyte analysis system 110 may include an alert service 140. The alert service 140 may generate an alert to an individual if an analyte is above or below a certain threshold. For example, for a potassium serum level, the individual may be alerted if the level is above 5. Furthermore, the alert service 140 may provide additional alerts to other individuals. For example, an alert may be provided to a doctor, a caretaker, a significant other, or the like.

Figure 2:
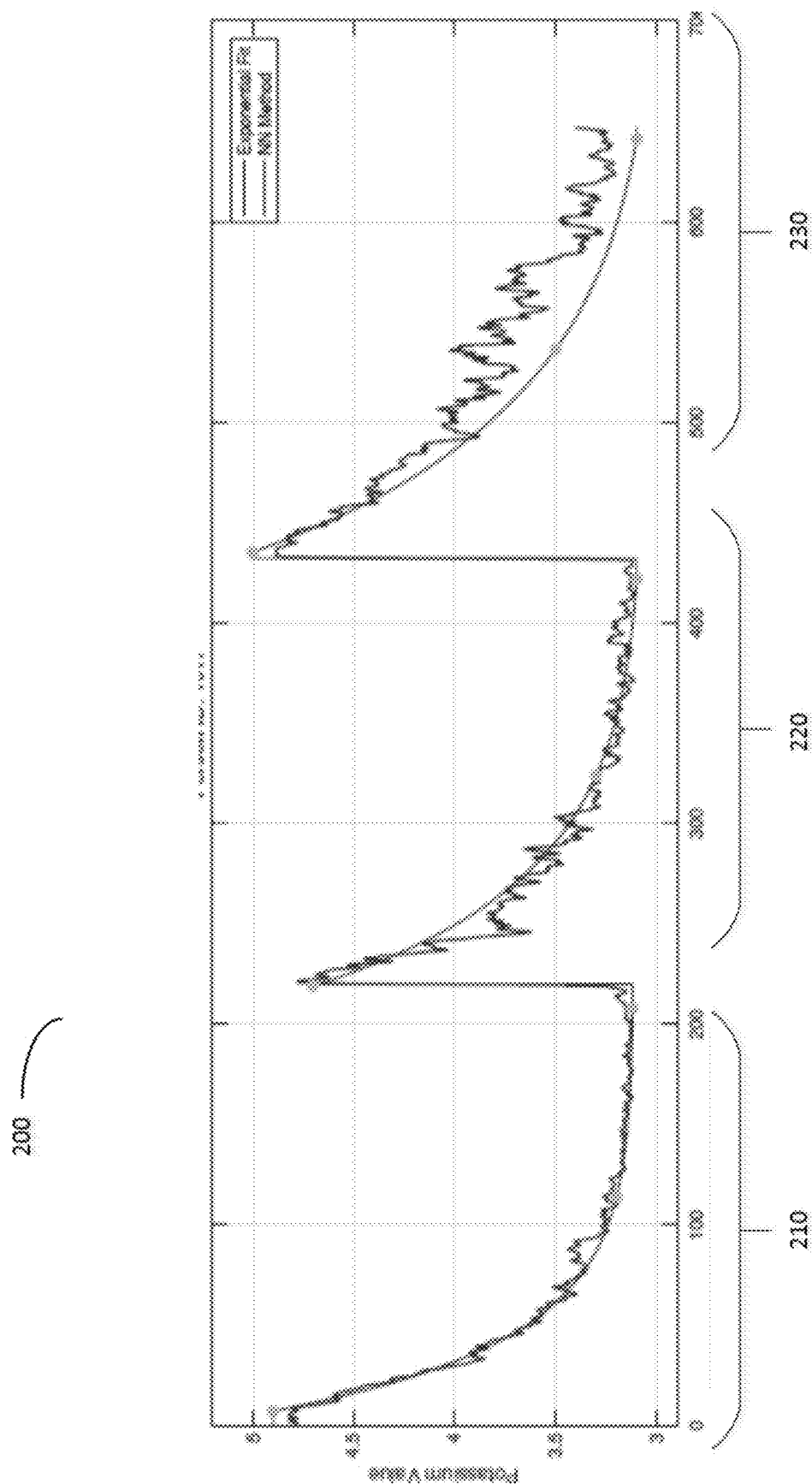
FIG. 2 illustrates example data generated by analyte measurement systems as discussed herein, according to aspects of the disclosure.

FIG. 2 shows an example output of an analyte measurement system as applied to electrocardiogram data for an individual. For example, the analyte measurement system used to generate the data in FIG. 2 may be the same or similar as the analyte measurement system 100 described with reference to FIG. 1.

The chart 200 shows the potassium value calculated via interpolation from blood tests, compared to the potassium value determined by the machine learning model. The first (leftmost) dialysis session 210 was used to generate training data for the machine learning model. The second dialysis session 220 and third dialysis sessions 230 show evaluation of the model generalized to data that it had not trained on. As shown in FIG. 2, the electrocardiogram data analyzed by the machine learning model in the second dialysis session 220 and the third dialysis session 230 represent accurately the potassium level of the individual's blood throughout the dialysis process. The machine learning model could further be used to provide analysis of the individual's potassium levels at points between dialysis sessions. Accordingly, the potassium level may be monitored for periods of high levels to reduce the risk to the individual between sessions.

Figure 3:
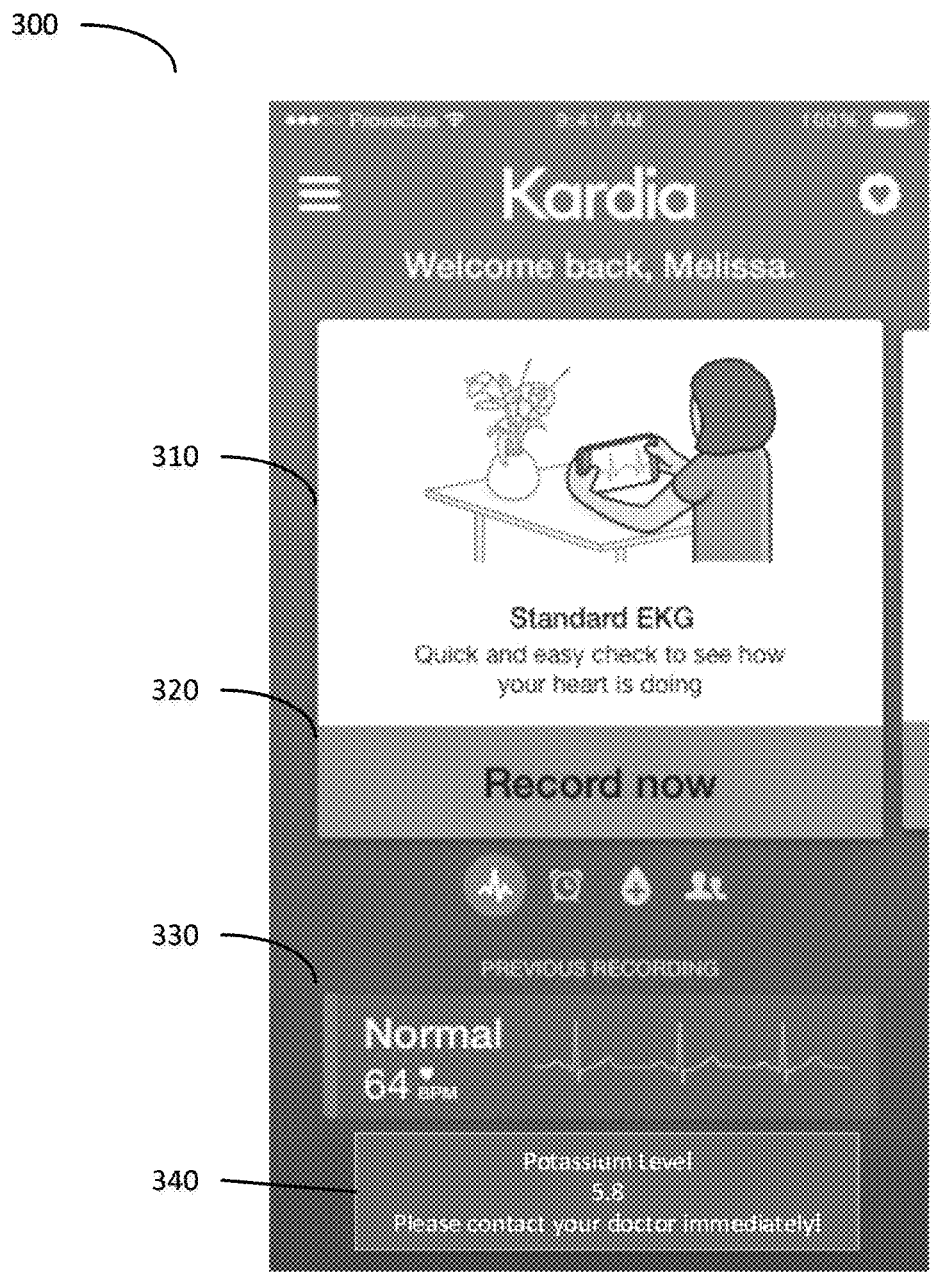
FIG. 3 illustrates an example user interface as generated by an analyte measurement system as discussed herein, according to aspects of the disclosure.

FIG. 3 depicts an example user interface 300 showing an analyte analysis as described herein. For example, in some embodiments the user interface 300 may be generated by user interface generator 135 as described in FIG. 1. The user interface 300, or variants thereof, may be displayed on a mobile device, a personal computer, a web browser, a smart watch, or other computing devices.

The user interface 300 includes an interface 310 prompting a user to perform a standard electrocardiogram. The user may have an option 320 to record the electrocardiogram with an electrocardiogram sensor is in place. The electrocardiogram 330 may be displayed as it is recorded by the individual. Furthermore, an output 340 of an analyte level of the individual may be provided. In some implementations, the electrocardiogram sensor may pass data to an electrocardiogram analyzer to apply a machine learning model as described above with respect to FIG. 1. In some embodiments, the electrocardiogram sensor may pass data along to a number of machine learning models to test additional analyte levels.

Based on the analyte levels, a user interface generator may generate an additional user interface element 340 that provide the analyte level. In some embodiments, a user interface generator may provide the analyte levels regardless of their range. An alert service may use the data provided by the machine learning model to determine whether to alert the individual to additional issues with potential analyte levels. For example, as shown in user interface element 340, in some embodiments, a user interface may provide an alert and a recommendation to contact a doctor or physician. In some embodiments, an alert service may request a retest of an electrocardiogram prior to providing an alert to contact a doctor or physician.

Figure 4:
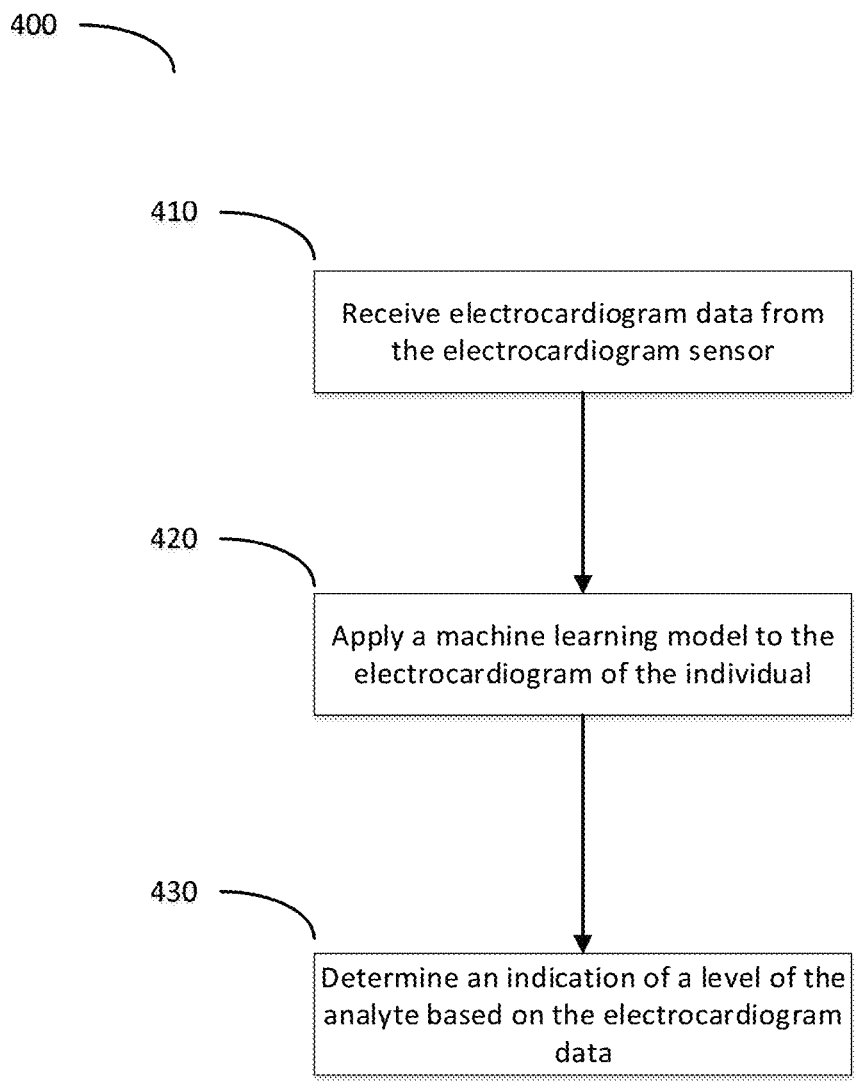
FIG. 4 illustrates flow diagram of processes as performed by an analyte measurement system, according to aspects of the disclosure.

FIG. 4 depicts a data flow 400 illustrating the application of a machine learning model to an electrocardiogram of a subject. In some embodiments, the processes described with respect to FIG. 4 may be performed by one or more components of the analyte measurement system 100 as described with reference to FIG. 1.

Beginning in block 410, an analyte measurement system may receive electrocardiogram data from the electrocardiogram sensor. For example, the electrocardiogram sensor may provide real-time data of an individual's heartbeats. In some embodiments, the electrocardiogram sensor may be a 1 lead sensor, a 2 lead sensor, a 3 lead sensor, a 4 lead sensor, a 6 lead sensor, or a 12 lead sensor. In some embodiments, the analyte measurement sensor may utilize only a subset of the electrocardiogram data that is received.

In block 420, the analyte measurement system may apply a machine learning model to the electrocardiogram of the individual. In some embodiments, the machine learning model has been trained based on previous electrocardiogram data associated with the subject and source of an analyte measurement associated with the subject as described above. For example, the machine learning model may be specific to the individual based on prior measurements.

In block 430, the analyte measurement system may determine an indication of a level of the analyte based on the electrocardiogram data. For example, the analyte measurement system may determine whether the individual's analyte levels for a target analyte are higher or lower than expected or healthy. Furthermore, the analyte measurement system may determine a specific estimated level of the individual's analyte levels, in some embodiments.

Figure 5:
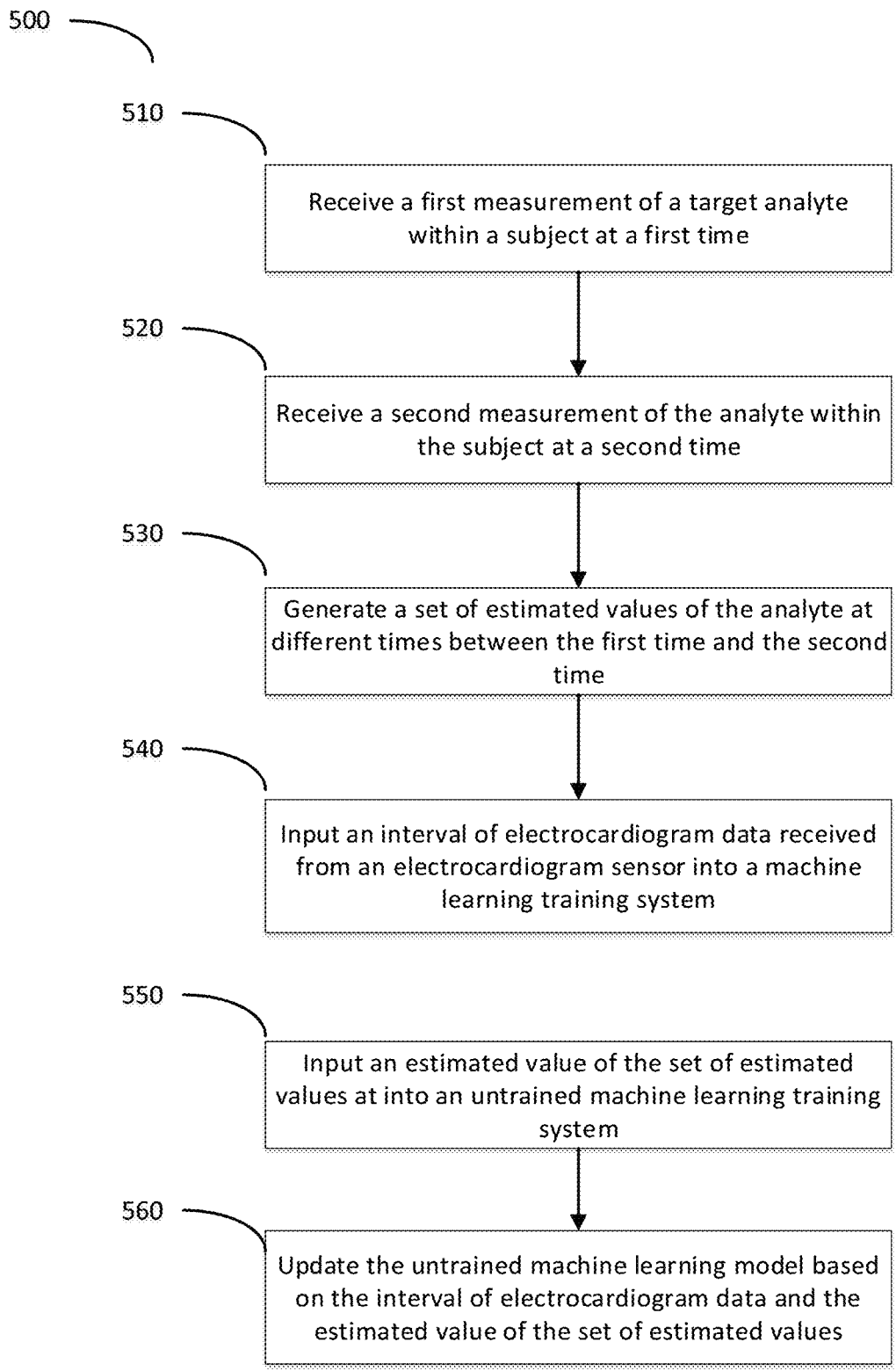
FIG. 5 illustrates flow diagram of processes as performed by an analyte measurement system, according to aspects of the disclosure.

FIG. 5 depicts a data flow 500 illustrating the application of a machine learning model to an electrocardiogram of a subject. In some embodiments, the processes described with respect to FIG. 5 may be performed by one or more components of the analyte measurement system 100 as described with reference to FIG. 1.

Beginning in block 510, an analyte measurement system may receive a first measurement of a target analyte within a subject at a first time. For example, a subject or individual may have a blood test run to determine a level of an analyte prior to performing a process or procedure.

In block 520, the analyte measurement system may receive a second measurement of the analyte within the subject at a second time. For example, a subject or individual may have a blood test run to determine a level of an analyte after performing a process or procedure. Although described as two measurements, in various embodiments, fewer or additional measurements may be used to determine analyte levels with additional accuracy.

In block 530, the analyte measurement system generates a set of estimated values of the analyte at different times between the first time and the second time. For example, a known model may be used to determine approximate analyte levels between a first time and a second time if both measurements at both times are known. In some embodiments, as discussed herein, additional measurements may be used to provide additional accuracy. Furthermore, in some embodiments, a single measurement could be taken, and an action performed in controlled circumstances, that causes an analyte level to vary in a predictable manner. For example, a measurement could be taken at the beginning of a dialysis session and additional values may be generated from the single measurement based on the individual's size, the equipment used, or other factors. In another embodiment, a specific drug may be administered that is known to accumulate in the bloodstream in a predictable manner over time. Similarly, ingestion of food may be used where the absorption of sugar, fats, proteins, vitamins, minerals, or the release of insulin or other enzymes or metabolites may be predictable in the blood stream.

In block 540, the analyte measurement system may input an interval of electrocardiogram data received from an electrocardiogram sensor into a machine learning training system. For example, the interval of electrocardiogram data may be taken at a third time between the first time and the second time.

In block 550, the analyte measurement system may input use an analyte level generated from the measured value (or values) of the analyte as a label input into an untrained machine learning training system. This may provide the training system with data to determine the accuracy of the machine learning model.

In block 560, the analyte measurement system may update the untrained machine learning model based on comparing an output of the machine learning training system based on the interval of electrocardiogram data and the estimated value of the set of estimated values at the third time. For example, the analyte measurement system may update weight matrices applied by a convolutional or recurrent machine learning models.

Figure 6:
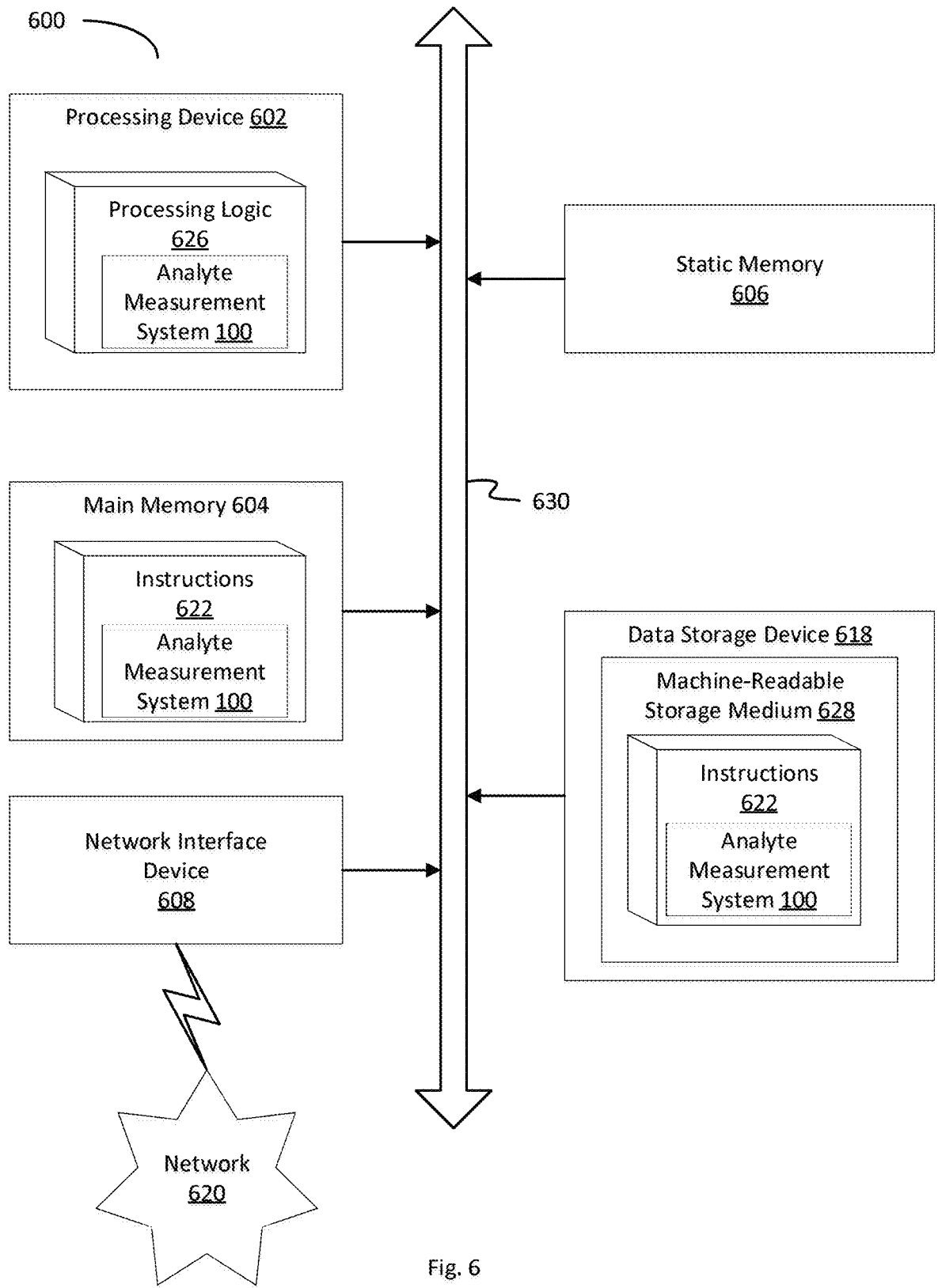
FIG. 6 illustrates an example computing environment of an analyte measurement system, according to aspects of the disclosure.

FIG. 6 illustrates a diagrammatic representation of a machine in the example form of a computer system 600 within which a set of instructions, for causing the machine to perform any one or more of the methodologies discussed herein, may be executed. In alternative embodiments, the machine may be connected (e.g., networked) to other machines in a local area network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, a switch or bridge, a hub, an access point, a network access control device, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. In one embodiment, computer system 600 may be representative of a server, such as one or more components of analyte measurement system 100 configured to perform processes as described above.

The exemplary computer system 600 includes a processing device 602, a main memory 604 (e.g., read-only memory (ROM), flash memory, dynamic random access memory (DRAM), a static memory 606 (e.g., flash memory, static random access memory (SRAM), etc.), and a data storage device 618, which communicate with each other via a bus 630. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Processing device 602 represents one or more general-purpose processing devices such as a microprocessor, central processing unit, or the like. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device 602 may also be one or more special-purpose processing devices such as an application specific integrated circuit (ASIC), a field programmable gate array (FPGA), a digital signal processor (DSP), network processor, or the like. The processing device 602 is configured to execute processing logic 626, which may be one example of system 400 shown in FIG. 4, for performing the operations and steps discussed herein.

The data storage device 618 may include a machine-readable storage medium 628, on which is stored one or more set of instructions 622 (e.g., software) embodying any one or more of the methodologies of functions described herein, including instructions to cause the processing device 602 to execute analyte measurement systems 100. The instructions 622 may also reside, completely or at least partially, within the main memory 604 or within the processing device 602 during execution thereof by the computer system 600; the main memory 604 and the processing device 602 also constituting machine-readable storage media. The instructions 622 may further be transmitted or received over a network 620 via the network interface device 608.

The machine-readable storage medium 628 may also be used to store instructions to perform a method for analyte measurement systems, as described herein. While the machine-readable storage medium 628 is shown in an exemplary embodiment to be a single medium, the term "machine-readable storage medium" should be taken to include a single medium or multiple media (e.g., a centralized or distributed database, or associated caches and servers) that store the one or more sets of instructions. A machine-readable medium includes any mechanism for storing information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; or another type of medium suitable for storing electronic instructions.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular embodiments may vary from these exemplary details and still be contemplated to be within the scope of the present disclosure.

Additionally, some embodiments may be practiced in distributed computing environments where the machine-readable medium is stored on and or executed by more than one computer system. In addition, the information transferred between computer systems may either be pulled or pushed across the communication medium connecting the computer systems.

Embodiments of the claimed subject matter include, but are not limited to, various operations described herein. These operations may be performed by hardware components, software, firmware, or a combination thereof.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent or alternating manner.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

It will be appreciated that variants of the above-disclosed and other features and functions, or alternatives thereof, may be combined into may other different systems or applications. Various presently unforeseen or unanticipated alternatives, modifications, variations, or improvements therein may be subsequently made by those skilled in the art which are also intended to be encompassed by the following claims. The claims may encompass embodiments in hardware, software, or a combination thereof

What is claimed is:

1. A system comprising:
   an electrocardiogram sensor; and
   at least a processing device operatively coupled to the electrocardiogram sensor, wherein the at least a processing device is configured to:
      train an untrained machine learning model, wherein training the untrained machine learning model comprises:
         receiving previous electrocardiogram data of a user from the electrocardiogram sensor;
         receiving a first measurement of a level of an analyte within the user at a first time;
         generating a set of estimated values of the level of the analyte in the user over a time period subsequent to the first time based in part on the level of the analyte within the user at the first time; and
         training the untrained machine learning model using the previous electrocardiogram data and one or more of the set of estimated values;
      receive current electrocardiogram data of the user from the electrocardiogram sensor;
      determine an indication of a current level of the analyte in the user based on the current electrocardiogram data using the trained machine learning model, wherein the current electrocardiogram data is provided to the trained machine learning model as an input to output the current level of the analyte in the user; and
      generate an alert to the user and a recommendation to contact a doctor or physician if the indication of the current level of the analyte in the user is above or below a threshold, wherein the at least a processor is further configured to, if the indication of the current level of the analyte in the user is above or below the threshold, provide a request to the user to retest the current electrocardiogram data.

2. The system of claim 1, wherein to train the untrained machine learning model, the at least a processing device is configured to:
   input an interval of electrocardiogram data of the previous electrocardiogram data received from the electrocardiogram sensor into the untrained machine learning model, wherein the interval of electrocardiogram data was measured by the electrocardiogram sensor during the time period subsequent to the first time; and
   update the untrained machine learning model based on a comparison of an output of the untrained machine learning model based on the interval of electrocardiogram data and the one or more estimated values of the set of estimated values of the level of the analyte in the user.

3. The system of claim 1, wherein the at least a processing device generates the set of estimated values of the level of the analyte in the user based further in part on data about an action that causes the level of the analyte in the user during the time period subsequent to the first time to vary in a predictable manner.

4. The system of claim 3, wherein the data comprises information about variance in the level of the analyte in the user after administration to the user of a drug that accumulates in a bloodstream of the user over time.

5. The system of claim 3, wherein the data comprises information about variance in the level of the analyte in the user while performing dialysis on the user.

6. The system of claim 1, wherein to train the untrained machine learning model, the at least a processing device is further configured to:
   receive a second measurement of the level of the analyte within the user at a second time.

7. The system of claim 6, wherein the at least a processing device generates the set of estimated values of the level of the analyte in the user based on the level of the analyte within the user at the first time and the level of the analyte within the user at the second time.

8. The system of claim 1, wherein the at least a processor is further configured to generate additional alerts to other individuals if the indication of the current level of the analyte in the user is above or below the threshold.

9. The system of claim 1, wherein the at least a processor is further configured to pre-process multiple electrocardiogram signals to form the previous electrocardiogram data that is used to train the untrained machine learning model.

10. The system of claim of claim 9, wherein the at least a processor is configured to pre-process the multiple electrocardiogram signals by:
averaging multiple electrocardiogram waveforms to form one or more sets of single averaged electrocardiogram waveforms; and
performing smoothing and/or noise reduction on the one or more single averaged electrocardiogram waveforms to generate one or more inputs that are used to train the untrained machine learning model.

11. A method comprising:
training, by a least a processing device, an untrained machine learning model, wherein training the untrained machine learning model comprises:
receiving previous electrocardiogram data of a user from an electrocardiogram sensor;
receiving a first measurement of a level of an analyte within the user at a first time;
generating a set of estimated values of the level of the analyte in the user over a time period subsequent to the first time based in part on the level of the analyte within the user at the first time; and
training the untrained machine learning model using the previous electrocardiogram data and one or more of the set of estimated values;
receiving, by the at least a processor, current electrocardiogram data of the user from the electrocardiogram sensor;
determining, by the at least a processor, an indication of a current level of the analyte in the user based on the current electrocardiogram data using the trained machine learning model, wherein the current electrocardiogram data is provided to the trained machine learning model as an input to output the current level of the analyte in the user; and
generating, by the at least a processing device, an alert to the user and a recommendation to contact a doctor or physician if the indication of the current level of the analyte in the user is above or below a threshold, wherein the at least a processor is further configured to, if the indication of the current level of the analyte in the user is above or below the threshold, provide a request to the user to retest the current electrocardiogram data.

12. The method of claim 11, wherein training the untrained machine learning model comprises:
inputting an interval of electrocardiogram data of the previous electrocardiogram data received from the electrocardiogram sensor into the untrained machine learning model, wherein the interval of electrocardiogram data was measured by the electrocardiogram sensor during the time period subsequent to the first time; and
updating the untrained machine learning model based on a comparison of an output of the untrained machine learning model based on the interval of electrocardiogram data and the one or more estimated values of the set of estimated values of the level of the analyte in the user.

13. The method of claim 11, wherein the set of estimated values of the level of the analyte in the user is generated based further in part on data about an action that causes the level of the analyte in the user during the time period subsequent to the first time to vary in a predictable manner.

14. The method of claim 13, wherein the data comprises information about variance in the level of the analyte in the user after administration to the user of a drug that accumulates in a bloodstream of the user over time.

15. The method of claim 13, wherein the data comprises information about variance in the level of the analyte in the user while performing dialysis on the user.

16. The method of claim 8, wherein training the untrained machine learning model further comprises:
receiving a second measurement of the level of the analyte within the user at a second time.

17. The method of claim 16, wherein the set of estimated values of the level of the analyte in the user is generated based on the level of the analyte within the user at the first time and the level of the analyte within the user at the second time.

18. A non-transitory computer-readable medium having instructions stored thereon which, when executed by at least a processing device, cause the at least a processing device to:
train an untrained machine learning model, wherein training the untrained machine learning model comprises:
receiving previous electrocardiogram data of a user from an electrocardiogram sensor; and
receiving a first measurement of a level of an analyte within the user at a first time;
generating a set of estimated values of the level of the analyte in the user over a time period subsequent to the first time based in part on the level of the analyte within the user at the first time; and
training the untrained machine learning model using the previous electrocardiogram data and one or more of the set of estimated values;
receive current electrocardiogram data of the user from the electrocardiogram sensor;
determine an indication of a current level of the analyte in the user based on the current electrocardiogram data using the trained machine learning model, wherein the current electrocardiogram data is provided to the trained machine learning model as an input to output the current level of the analyte in the user; and
generate an alert to the user and a recommendation to contact a doctor or physician if the indication of the current level of the analyte in the user is above or below a threshold, wherein if the indication of the current level of the analyte in the user is above or below the threshold, provide a request to the user to retest the current electrocardiogram data.

* * * * *